United States Patent [19]

Brugger

[11] Patent Number: 5,674,199
[45] Date of Patent: Oct. 7, 1997

[54] TOP FLOW BUBBLE TRAP METHOD

[75] Inventor: James Myron Brugger, Salisbury, Mass.

[73] Assignee: Cobe Laboratories, Inc., Arvada, Colo.

[21] Appl. No.: 531,784

[22] Filed: Sep. 21, 1995

Related U.S. Application Data

[63] Continuation of Ser. No. 158,930, Nov. 29, 1993, Pat. No. 5,503,801.

[51] Int. Cl.$^6$ .......................... B01D 9/00; A61M 1/14; A61M 3/00
[52] U.S. Cl. .................. 604/122; 604/4; 422/44; 95/260
[58] Field of Search .................. 422/44; 604/4, 604/29, 83, 80, 52, 122; 95/260; 210/239; 96/197, 204; 128/DIG. 3

[56] References Cited

U.S. PATENT DOCUMENTS

| | | | |
|---|---|---|---|
| 2,123,809 | 7/1938 | Seitz | 137/592 |
| 2,186,987 | 1/1940 | Nesset | 210/94 |
| 2,528,737 | 11/1950 | Butler | 604/406 |
| 2,586,513 | 2/1952 | Butler | 210/94 |
| 2,675,000 | 4/1954 | Ford | 604/252 |
| 2,693,189 | 11/1954 | Ryan | 604/408 |
| 2,696,818 | 12/1954 | Loghem | 604/252 |
| 2,729,212 | 1/1956 | Butler | 604/251 |
| 2,864,406 | 12/1958 | Schewel | 239/505 |
| 3,045,872 | 7/1962 | Hronas et al. | 222/146.2 |
| 3,221,996 | 12/1965 | Emmert et al. | 239/542 |
| 3,332,418 | 7/1967 | Brody | 604/86 |
| 3,340,871 | 9/1967 | Jellies | 604/251 |
| 3,744,492 | 7/1973 | Leibinsohn | 604/252 |
| 3,778,973 | 12/1973 | Martinez | 96/155 |
| 3,834,386 | 9/1974 | Sisley | 604/25 |
| 3,965,895 | 6/1976 | Dabney | 604/127 |
| 3,993,066 | 11/1976 | Virag | 604/52 |
| 4,013,072 | 3/1977 | Jess | 604/252 |
| 4,061,031 | 12/1977 | Grimsrud | 73/200 |
| 4,102,655 | 7/1978 | Jeffery et al. | 55/201 |
| 4,293,413 | 10/1981 | Schnell | 210/188 |
| 4,344,777 | 8/1982 | Siposs | 96/206 |
| 4,368,118 | 1/1983 | Siposs | 96/206 |

(List continued on next page.)

FOREIGN PATENT DOCUMENTS

| | | |
|---|---|---|
| 0058325 B1 | 3/1982 | European Pat. Off. . |
| 146708 A2 | 7/1985 | European Pat. Off. . |
| 1171047 | 1/1960 | France . |
| 3202582 A1 | 9/1982 | Germany . |
| 3720844 A1 | 1/1989 | Germany . |
| 57-176370 | 10/1983 | Japan . |
| 854398 | 8/1981 | U.S.S.R. . |

*Primary Examiner*—Nina Bhat
*Attorney, Agent, or Firm*—Carol W. Burton; Holland & Hart LLP

[57] ABSTRACT

An apparatus for trapping bubbles in blood flowing in a circuit, such as blood in an extracorporeal circuit, is provided. The apparatus includes a housing which defines a substantially vertical chamber. Blood is introduced into the chamber through an inlet tube extending downwardly into the chamber and is removed from the chamber at an exit port near the lower end of the housing. A diverter having a container base and rim is positioned within the chamber. Blood is introduced near the container base. The blood is redirected upward upon contact with the container base and is then redirected downward over the rim. The redirection of blood flow provides an opportunity for bubbles in the blood to separate from the blood in the chamber and also helps prevent stagnation of blood in the chamber which might otherwise lead to clotting and separation of the blood.

Blood is introduced into a chamber of the apparatus in a generally downward direction below the level of blood already present in the chamber. The blood is then directed in a generally upward direction, after which it is redirected in a generally downward direction. The reversal of blood flow provides an opportunity for bubbles in the blood to separate from the blood. Thereafter the blood and bubbles are collected.

6 Claims, 4 Drawing Sheets

U.S. PATENT DOCUMENTS

| | | | |
|---|---|---|---|
| 4,395,260 | 7/1983 | Todd et al. | 604/122 |
| 4,428,743 | 1/1984 | Heck | 604/4 |
| 4,493,705 | 1/1985 | Gordon | 604/122 |
| 4,547,190 | 10/1985 | Leason | 604/185 |
| 4,568,330 | 2/1986 | Kujawski et al. | 604/53 |
| 4,601,712 | 7/1986 | Cole et al. | 604/251 |
| 4,622,032 | 11/1986 | Katsura | 604/122 |
| 4,643,713 | 2/1987 | Viitala | 604/4 |
| 4,666,598 | 5/1987 | Heath et al. | 210/239 |
| 4,681,606 | 7/1987 | Swan, Jr. et al. | 55/193 |
| 4,734,269 | 3/1988 | Clarke | 95/156 |
| 4,806,135 | 2/1989 | Siposs | 96/212 |
| 4,863,452 | 9/1989 | Irmiter | 604/408 |
| 4,900,308 | 2/1990 | Verkaart | 604/126 |
| 4,964,984 | 10/1990 | Reeder et al. | 210/188 |
| 5,061,236 | 10/1991 | Sutherland | 604/4 |
| 5,102,400 | 4/1992 | Leibinsohn | 604/251 |
| 5,120,302 | 6/1992 | Vescovini | 604/4 |
| 5,328,461 | 7/1994 | Utterberg | 604/80 |
| 5,330,425 | 7/1994 | Utterberg | 604/83 |

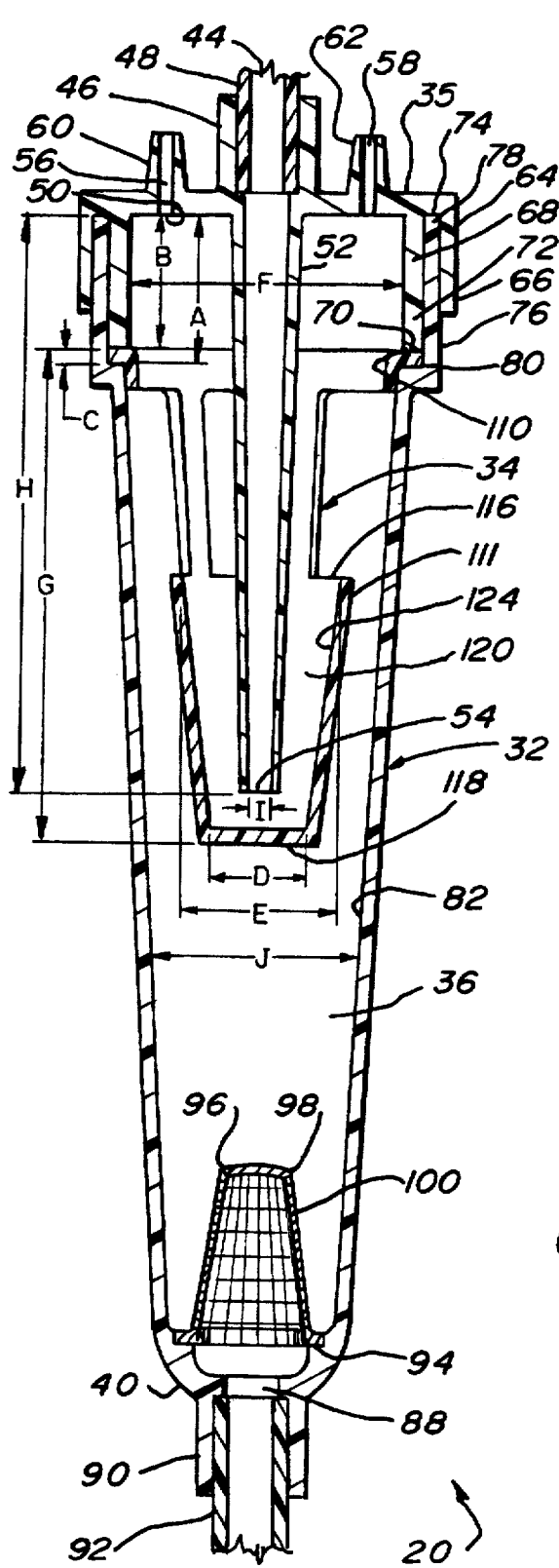
Fig_5
Fig_3

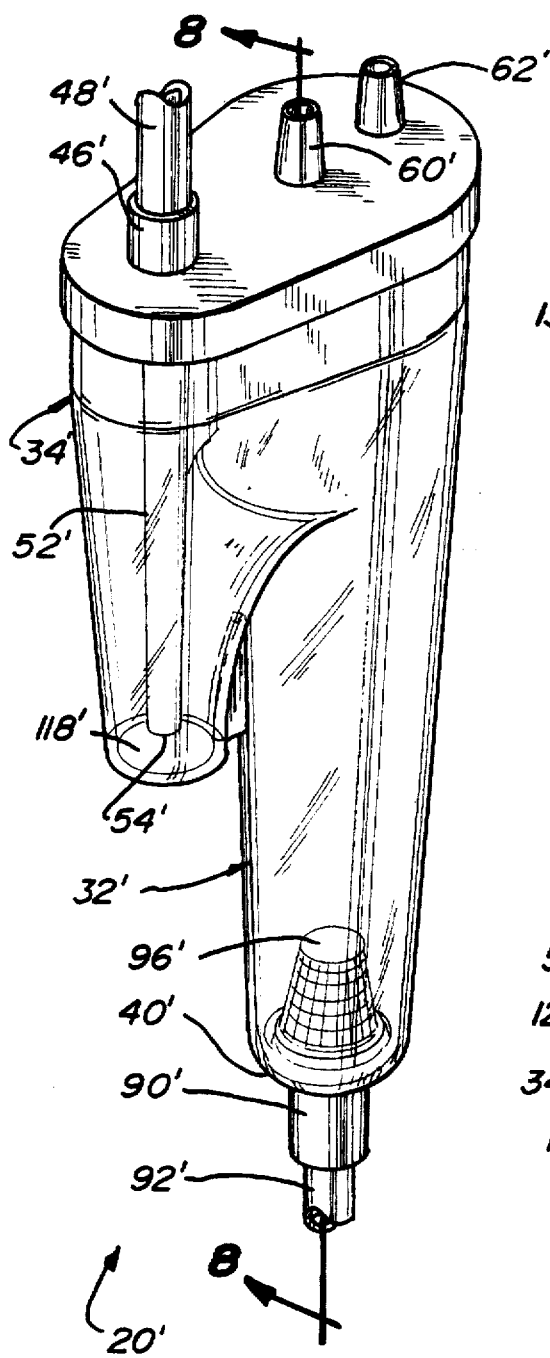
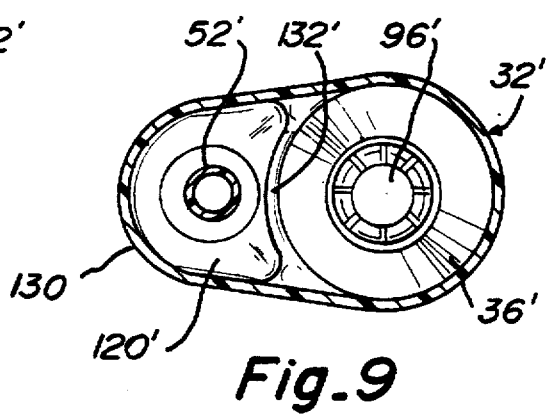
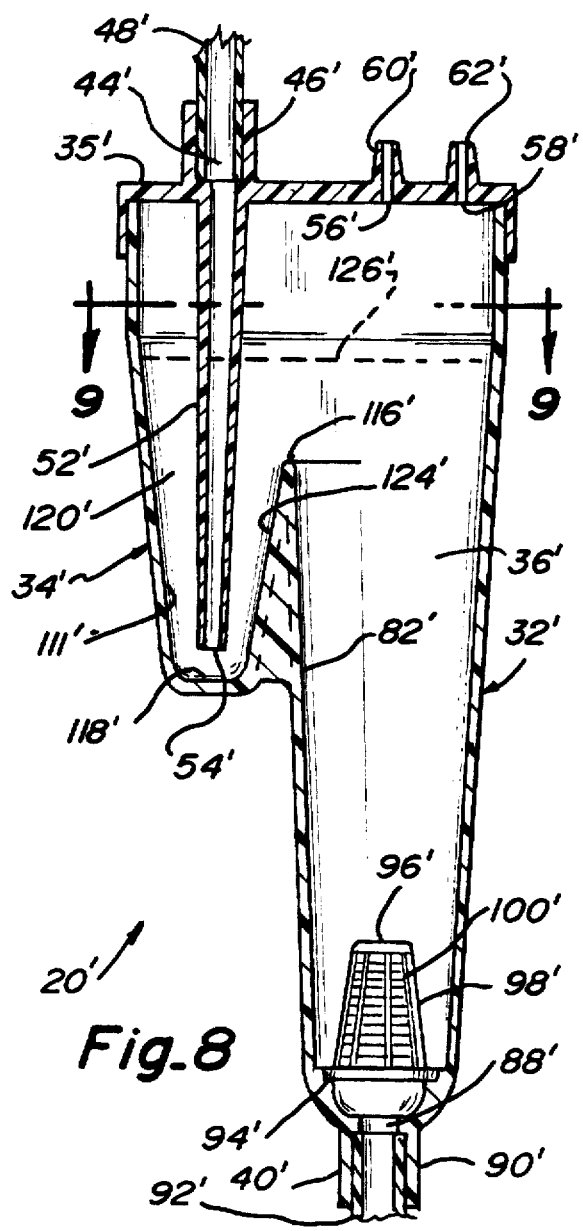
Fig. 7
Fig. 9
Fig. 8

TOP FLOW BUBBLE TRAP METHOD

CROSS REFERENCE TO RELATED APPLICATION

This application is a continuation of U.S. patent application Ser. No. 08/158,930 for TOP FLOW BUBBLE TRAP APPARATUS AND METHOD, filed Nov. 29, 1993 now U.S. Pat. No. 5,503,801 and assigned to the Assignee hereof, the disclosure of which is incorporated herein by reference.

FIELD OF THE INVENTION

This invention relates to bubble trap apparatus and method for the extracorporeal treatment of blood. More particularly this invention relates to new and improved bubble trap apparatus and method that aid in the removal of bubbles from blood and in the prevention of the formation of bubbles in the blood during its extracorporeal treatment.

BACKGROUND OF THE INVENTION

Extracorporeal blood treatment involves removing blood from a patient, treating the blood external to the patient and returning the treated blood to the patient. Occasionally, bubbles form in the blood during extracorporeal blood treatment as a result of leakage of air into the blood at the point blood is withdrawn from the patient for extracorporeal treatment and as a result of leakage of air at points of connection in the extracorporeal treatment system. Bubbles also form as a result of turbulence of the blood flowing in the extracorporeal treatment system and coalescence of gases in the blood during treatment, among other causes. Care must be taken to remove bubbles in the blood prior to returning the blood to the patient and, to the extent possible, prevent formation of bubbles in the blood during treatment. Blood returned to the patient which contains bubbles creates a risk of serious health consequences to the patient.

Sometimes bubbles in blood flowing through extracorporeal treatment systems are optically and sonically detectable and many such systems incorporate equipment capable of detecting these bubbles. When bubbles are detected, the flow of blood returning to the patient is usually halted to prevent return of the detected bubbles to the patient. However, it is preferable that such bubbles be collected and removed from the blood so that blood treatment can continue uninterrupted.

Most extracorporeal treatment systems incorporate chambers for removal of bubbles from the blood undergoing treatment. These chambers, often referred to as bubble traps, provide an opportunity for bubbles in the blood to separate from the liquid while the blood is in the chamber. Bubbles in the blood rise to the surface of the blood in the chamber. The gas from the bubbles which collects above the level of liquid is mechanically removed from the chamber, or is allowed to remain in the chamber until extracorporeal treatment is complete.

It is possible, however, that smaller bubbles may be present in the blood which may not be collected in the bubble traps of some extracorporeal treatment systems. The patient may then be subject to a risk of injury when these smaller bubbles coalesce into a larger bubble upon aggregation of the bubbles within the patient or may be subject to other risks.

Conditions under which bubbles form in the blood during extracorporeal treatment may be exacerbated by higher blood flow rates. For example, blood entering a bubble trap apparatus at a high rate may froth and create bubbles in the blood present in the bubble trap apparatus. These bubbles could pass through the bubble trap apparatus and remain in the blood to be returned to the patient.

Poor flow patterns can also create problems for blood flowing through a bubble trap apparatus. For example, if blood flow in a bubble trap apparatus is excessively turbulent, the blood's clotting processes may be activated undesireably and blood clots may form in the blood. Also by way of example, incomplete mixing of blood can cause blood in portions of the bubble trap apparatus to stagnate. The stagnated blood is then susceptible to clotting. Clotting of blood in a bubble trap apparatus may result in occlusion of lines of the extracorporeal blood treatment system or injury to the patient.

When blood is introduced into a bubble apparatus 8 below the upper surface of the blood already present in the apparatus, stagnation and clotting have a tendency to occur in the blood near the upper surface of the blood. Stagnation and clotting occur near the upper surface of blood because the newly introduced blood tends to flow downward and often does not mix with blood above the point of introduction and near the upper surface. Although the resulting clots may be filtered out of the blood before the blood is returned to the patient, excessive clot formation can occlude filters, which can lead to decreased blood flow to the patient.

One way that clot formation has been minimized is by introducing additional heparin into the blood of the patient. However, excess heparin in a patient can lead to other health problems and therefore excessive use of heparin is not preferred.

It is against this background that the significant improvements and advancements of the present invention have taken place.

SUMMARY OF THE INVENTION

One important aspect of the present invention relates to a bubble trap apparatus in which large and small bubbles are more expeditiously removed from blood while the blood is being treated extracorporeally. Another important aspect of the present invention relates to the minimization of bubble formation during such treatment. Still another important aspect is to maintain blood flow throughout the apparatus and thereby reduce the risks of forming blood clots.

In accordance with these and other aspects, the present invention relates to an apparatus for trapping bubbles in blood flowing in a circuit, for example an extracorporeal blood treatment circuit, which comprises a housing defining a substantially vertical chamber through which the blood flows. Blood is introduced to the apparatus through an inlet port near the upper end of the housing. An elongated tube surrounds the inlet port and extends downward therefrom to introduce blood into the chamber. A diverter is positioned within the chamber and includes a container having a rim. The elongated tube is disposed within the container to cause blood introduced into the chamber to first flow into the container, fill the container and then flow over the rim into the chamber. The blood reverses its direction of flow as it leaves the inlet tube and fills the container and again reverses it direction of flow as it passes over the rim and flows down through the chamber. This flow reversal gives gas in the blood a chance to coalesce into bubbles and give these and other bubbles in the blood an opportunity to rise to the surface of the blood in the chamber and separate from the blood. Thereafter, the blood exits the chamber out an exit port in the housing.

In accordance with other aspects, the present invention relates to a method for separating bubbles in blood flowing through an apparatus, such as an extracorporeal blood treatment system. Blood is introduced into a chamber of the apparatus in a generally downward direction below the level of blood already present in the chamber. The blood is then directed in a generally upward direction, after which it is redirected downward, to allow gases in the blood to coalesce into bubbles and to allow these and other bubbles in the blood an opportunity to rise to the surface of the blood and separate from the blood. Thereafter the blood is removed from the chamber at the lower end thereof.

These and other features of the present invention can be better understood from the following detailed description of a preferred embodiment of the present invention, taken in conjunction with the accompanying drawings that are briefly described below.

BRIEF DESCRIPTION OF THE DRAWINGS

FIG. 3 is an exploded view of the components of the bubble trap apparatus shown in FIG. 2.

FIG. 5 is an enlarged section view of the bubble trap apparatus taken substantially along line 5—5 in FIG. 2.

FIG. 7 is a perspective view of another embodiment of the bubble trap apparatus which is an alternative to that shown in FIG. 2.

FIG. 8 is a section view taken substantially along the line 8—8 in FIG. 7.

FIG. 9 is a section view taken substantially along the line 9—9 in FIG. 8.

DETAILED DESCRIPTION

Two presently preferred embodiments of apparatus 20 and 20' for collecting bubbles in blood undergoing extracorporeal treatment are shown in FIGS. 2 through 9. One bubble trap apparatus 20 or 20' is typically used as a component of an otherwise conventional extracorporeal treatment system 24, shown in FIG. 1.

Figure 1:
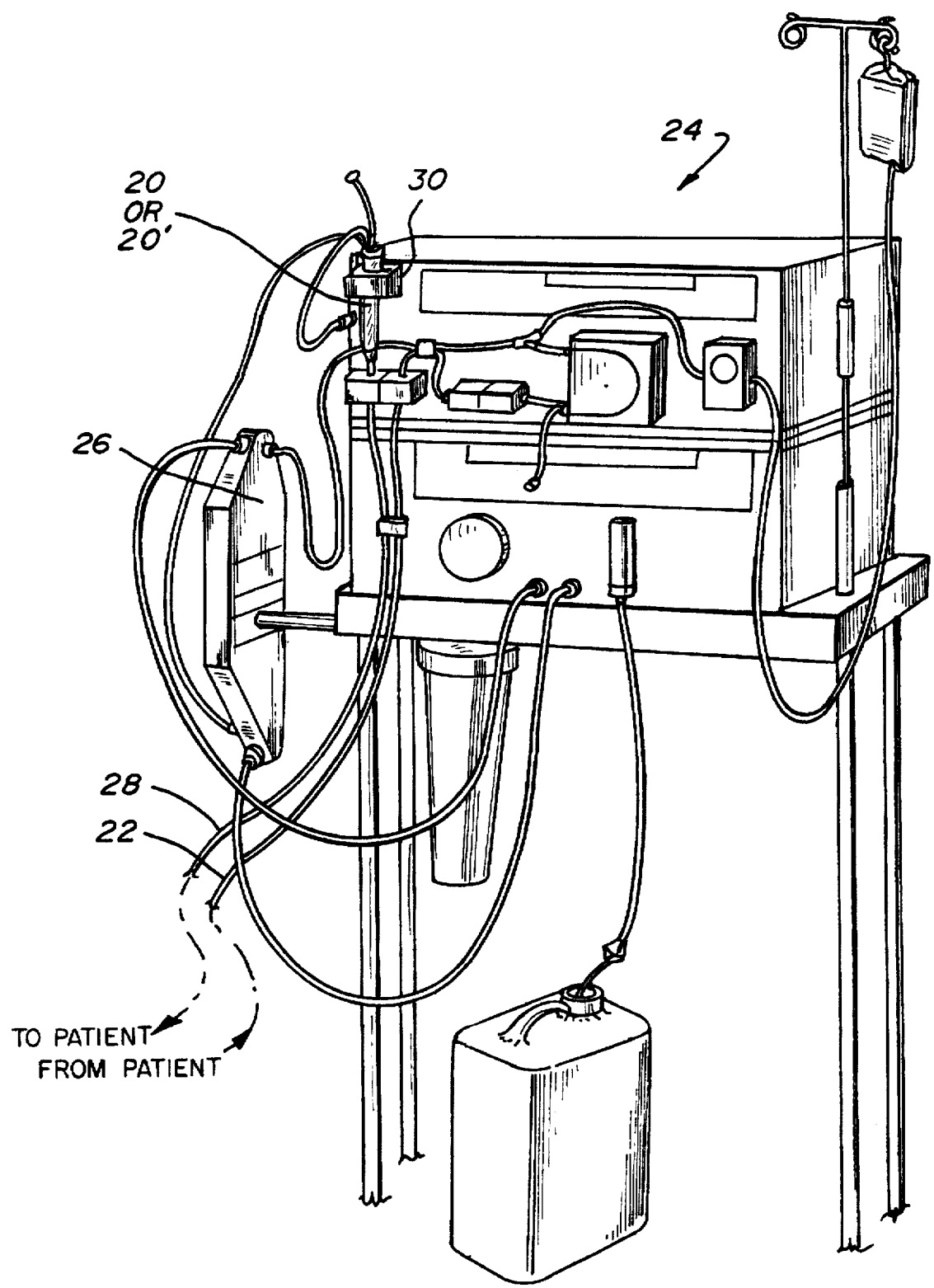
FIG. 1 is a perspective view of an extracorporeal blood treatment system to which a patient undergoing blood treatment is connected, utilizing a bubble trap apparatus incorporating the present invention.

Referring to FIG. 1, blood from a patient is circulated through conduit 22 to an extracorporeal treatment system 24 having a filtration unit 26 through which the blood flows. After passing through the filtration unit 26 the blood passes through the bubble trap apparatus 20 or 20' attached to the extracorporeal treatment system 24, after which the blood is returned to the patient via a return conduit 28. A blood level detection device 30 of the extracorporeal treatment system 24 is operatively positioned relative to the apparatus 20 or 20' for detecting changes in the level of blood in the apparatus 20 or 20' after filtration of the blood in the filtration unit 26 and after addition of any additional fluid or materials, but before return of the blood to the patient.

Figure 2:
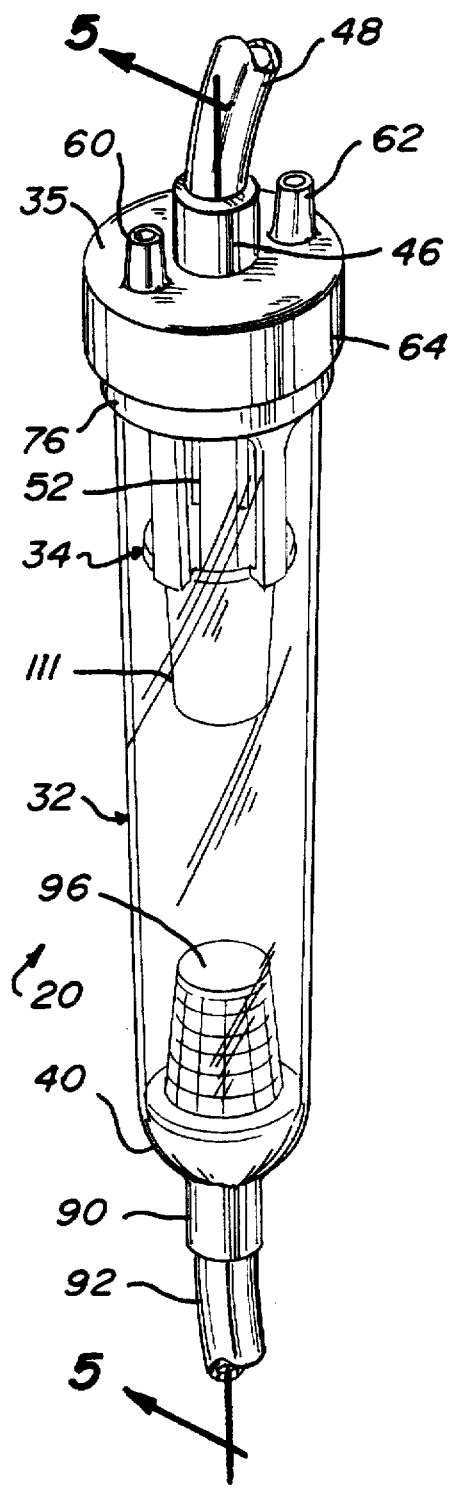
FIG. 2 is a perspective view of the bubble trap apparatus shown in FIG. 1.
Figure 4:
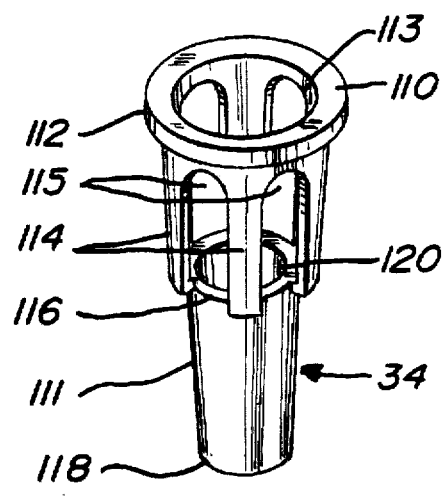
FIG. 4 is an enlarged perspective view of a diverter of the bubble trap apparatus shown in FIGS. 2 and 3.

Referring now to FIGS. 2 and 3, the bubble trap apparatus 20 comprises three primary components; a housing 32, a diverter 34 and a cap 35. The housing 32 defines a primary chamber 36 into which blood undergoing extracorporeal treatment is introduced. The diverter 34 is positioned within the primary chamber 36 and diverts and redirects blood flow within the primary chamber 36. The cap 35 covers the housing 32 and introduces blood into the diverter 34 for diversion within the primary chamber 36.

As is shown in FIGS. 2, 3 and 5, the housing 32 is generally of a substantially frustoconical shape and is tapered from the upper end 38 (FIG. 3) to the lower end 40 thereof. The cap 35 covers the upper end 38 of the housing 32 and has an inlet port 44 formed in the center thereof through which blood is introduced into the primary chamber 36. Extending upward from the center of the cap 35 around the perimeter of the inlet port 44 is an inlet coupling 46. The inner diameter of the inlet coupling 46 is such that the inlet coupling 46 surrounds and frictionally engages an outer circumferential rim 47 (FIG. 5) of an inlet conduit 48. The inlet conduit 48 is solvent bonded to the inlet coupling 46 to prevent dislocation of the inlet conduit 48 and to maintain fluid communication between the apparatus 20 and the extracorporeal treatment system 24 (FIG. 1).

Depending centrally from the inside surface 50 of the cap 35 is a hollow inlet tube 52 which terminates at a tip 54. The inlet tube 52 is in fluid communication with the inlet conduit 48 and directs blood flowing from the inlet conduit 48 out the tip 54 and into the primary chamber 36. The tip 54 is positioned at a predetermined point within the primary chamber 36.

Also formed in the cap 35 are first and second apertures 56 and 58 (FIG. 5). Surrounding the first aperture 56 is a portion of the cap 35 which extends upward to form a first coupling 60. A conduit or a measuring device (neither shown) may be attached to the first coupling 60 for measuring gas pressure or other characteristics of the contents of the primary chamber 36, for removal of materials from the primary chamber 36 for testing or other purposes, or for removal of gases which have collected in the primary chamber 36.

Surrounding the second aperture 58 is a portion of the cap 35 which extends upward to form a second coupling 62. A conduit (not shown) may be attached to the second coupling 62 for introduction of material and fluids, such as medication, into the primary chamber 36 and subsequent dissemination in the contents of the primary chamber.

In the side 64 of the cap 35 is former an outer lip 66 and an inner lip 68. The inner lip 68 is substantially parallel to and spaced apart from the outer lip 66 and has an inner lip end 70. The outer lip 66 and inner lip 68 define a channel 72 therebetween. The channel 72 terminates at a channel end 74. The upper end 38 of the housing 32 is receivably retained in the channel 72 between the outer and inner lips 66 and 68 respectively. The upper end 38 of the housing is solvent bonded to the cap 35, so that after assembly of the bubble trap apparatus 20 and during extracorporeal treatment when the bubble trap apparatus 20 is installed in an extracorporeal treatment system 24, the cap 35 and the housing 32 function in a unitary manner.

As is shown in FIG. 3, a circumferential band 76 having a rim 78 is formed at the upper end 38 of the housing 32. The band 76 extends above an upper seat 80 formed in the housing 32 at a point where the diameter of the housing 32 decreases. The inside length "A" (FIG. 5) of the band 76 is predetermined to be slightly longer than the length "B" (FIG. 5) of the inner lip 68, so that when the cap 35 is installed on the upper end 38 of the housing 32, the rim 78 of the band 76 will be adjacent to the end 74 of the channel 72 and the end 70 of the inner lip 68 will be spaced apart a distance "C" (FIG. 5) from the upper seat 80.

Below the seat 80, the inner housing wall 82 smoothly tapers towards the lower end 40 of the housing 32. Formed in the center of lower end 40 is an exit port 88 out of which blood exits the primary chamber 36. Depending from the center of the lower end 40 of the housing 32 and encircling the exit port 88 is an exit coupling 90. The inner diameter of the exit coupling 90 is predetermined to frictionally engage and receivably retain an exit conduit 92. The exit conduit 92 is further prevented from dislocation by creation of a solvent bond between the exit conduit 92 and the exit coupling 90.

A lower seat 94 is formed along the lower end 40 of the housing 32. The diameter of the lower seat 94 is predetermined to receive a filter 96. The filter 96 is formed in the shape of a hollow, truncated cone. Perforations 100 are formed in the side 98 of the filter 96. The perforations 100 allow blood to pass from the primary chamber 36, through the filter 96, out the exit port 88 and into the exit conduit 92, and are small enough to block particulate matter larger than a predetermined size, such as blood clots and foreign material, from passing into the exit conduit 92 and returning to the patient.

As shown in FIGS. 2–5, the diverter 34 is disposed within the primary chamber 36 to divert blood flow in the primary chamber 36. The diverter 34 comprises an annular collar 110 and a container 111. The collar 110 has an outer edge 112 and an inner edge 113. The container 111 is attached to the collar 110 by one or more, preferably four, connectors 114. Each connector 114 is relatively narrow so as to define relatively larger interconnector gaps 115 around the diverter 34. The connectors 114 are attached to the collar 110 away from the outer edge 112 and nearer or flush with the inside edge 113. The connectors 114 attach to the container 111 at an annular peripheral rim 116 of the container. The container 111 is of a slightly tapered pail-like shape (i.e. a hollow truncated cone), with the inside diameter "D" (FIG. 5) of the container base 118 being less than the inside diameter "E" (FIG. 5) of the container rim 116.

The diameter "F" (FIG. 5) of the collar 110 at the outer edge 112 thereof is approximately the same as the inside diameter of the housing band 76. The thickness of the collar 110 is approximately the same as the distance "C" described above. These dimensions permit the collar 110 to rest upon the upper seat 80 with the inner lip 68 resting in turn on the collar 110. This creates a sandwich effect which prevents undesirable movement of the diverter 34 within the primary chamber 36. When constructed in compliance with the dimensions "A" to "F", the collar 110, in cooperation with the inner lip 68, caps the primary chamber 36, thereby helping to prevent blood and other contents of the primary chamber 36 from leaking between the housing 32 and the cap 35 and helping to prevent gas and contaminants from being inadvertently introduced into the blood flowing through the bubble trap apparatus 20.

A height "G" (FIG. 5) of the diverter 34 is predetermined so that the combination of the height "G" and the length "B" of the inner lip is slightly greater than the length "H" (FIG. 5) of the inlet tube 52. When the components of the apparatus 20 are manufactured in compliance with these dimensions, the tip 54 of the inlet tube 52 is disposed above and adjacent to, but not touching, the center of the container base 118 when the diverter 34 is installed in the primary chamber 36 of the housing 32. Blood flowing in the inlet conduit 48 flows into the inlet tube 52, out the tip 54 and is directed into the container 111.

The container 111 defines a secondary chamber within the primary chamber 36 when the container 111 is installed in the primary chamber 36. The secondary chamber 120 is in fluid communication with the primary chamber 36. Fluid communication is achieved between the primary and secondary chambers 36 and 120 during operation of the bubble trap apparatus 20 when blood which has been directed out the tip 54 of the inlet tube 52 into the secondary chamber 120 fills the secondary chamber 120, flows through the interconnector gaps and over the container rim 116 into the primary chamber 36 between the inner wall 82 of the housing 32 and the outer wall 122 of the container 111, down through the primary chamber 36, through the perforations 100 of the filter 96, through the exit port 88 and into the exit conduit 92.

Figure 6:
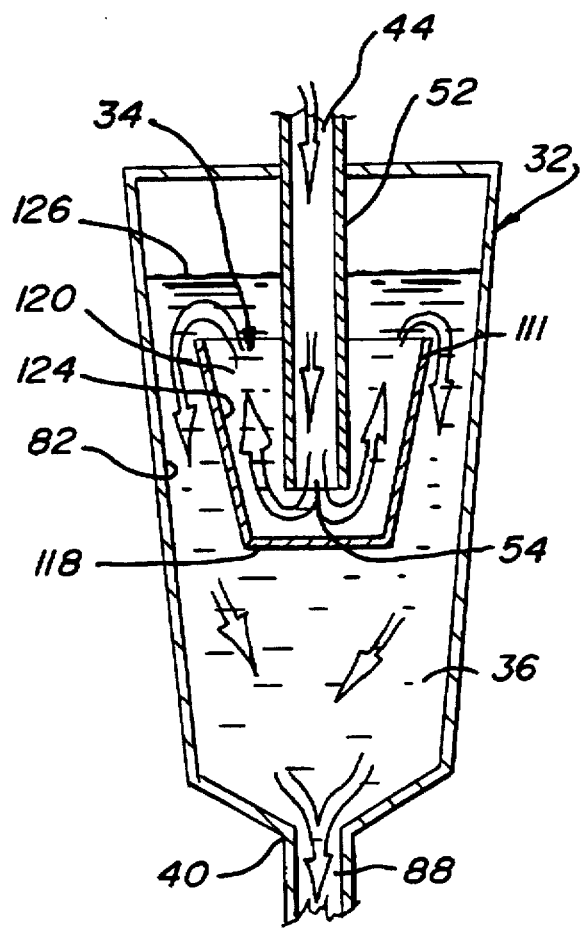
FIG. 6 is a generalized illustration related to FIG. 5 illustrating blood flow.

Diversion and redirection of the blood as it passes through the bubble trap apparatus 20 by the diverter 34 is better understood by referring to FIG. 6. Blood undergoing extracorporeal treatment flows past the inlet port 44 and through the inlet tube 52. The blood exits the inlet tube 52 out of the tip 54 and into the secondary chamber 120. Then, because the container 111 is closed at its base 118, blood is directed upward towards the rim 116 of the container. Blood is directed upward by deflection from the container base 118 and the inner wall 124 of the container 111, by the force of blood newly exiting the inlet tube tip 54 pushing from behind, and by laminar flow forces of blood already present in the container. The diameter "D" of the container base 118 and the obtuse angle of incidence of the inner wall 124 of the container 111 with the container base are both predetermined to cause blood entering the container 111 from the inlet tube tip 54 to reflect off of the container base 118 and the inner wall 124 and flow upwards rather than pooling in the container, thereby helping to prevent stagnation of blood within the container 111.

As the blood begins to flow upward through the secondary chamber 120, its flow rate decreases due to the increasing diameter of the secondary chamber 120 from the base 118 to the rim 116. This decreasing blood flow rate gives bubbles in the blood time to rise to the surface 126 of blood within the primary chamber 36 (FIG. 6). As the blood flows upward through the secondary chamber 120, gases in the blood are provided an opportunity to coalesce and then rise to the surface 126, to collect above the surface 126 for removal from the blood.

After the blood reaches the container rim 116, the blood flows over the rim 116 and is urged downward by gravitational forces into the primary chamber 36 of the housing 32 and down through the primary chamber to the outlet port 88. Because the average inside, diameter of the primary chamber 36 is greater than the diameter of the secondary chamber 120 at the rim 116, the blood flow rate may decrease further as the blood flows over the rim 116 and down through the primary chamber. The reduction of blood flow and the slower flow rate gives bubbles in the blood a further opportunity to rise to the surface 126 of the blood in the primary chamber 36 and gas in the blood has a further opportunity to coalesce and form bubbles. In addition, the tapered frustoconical shape of the primary chamber 36 helps prevent stagnation of blood and/or clotting of blood while in the primary chamber 36 because it contains no pockets in which blood may pool.

In operation, it is preferred that the upper blood surface 126 in the primary chamber 36 be maintained at a level substantially above the container rim 116. This allows blood introduced out of the tip 54 of the inlet tube 52 into the container 111 to flow upward over the container rim 116 in a sufficiently large flow path to maintain a slower blood flow rate while flowing through the interconnector gaps 115 and over the container rim 116. Moreover, when the blood surface 126 is maintained substantially above the container rim 116, blood does not splatter when flowing over the container rim 116 and falling to meet a blood level below the container rim 116. Such splattering can create substantial frothing, which is indicative of bubble formation.

The blood surface 126 in the bubble trap apparatus 20 is preferably maintained above the container rim 116 and below the annular collar 110 of the diverter 34. With this fluid level arrangement, the portion of the primary chamber 36 which is above the blood surface 126 provides space in which bubbles in the blood can collect after having risen to the surface 126 of the blood.

Initially, the desired level of the blood surface 126 in the primary chamber 36 is obtained by partially or fully occluding the exit conduit 92, allowing blood which is flowing first from the inlet tube 52 to fill the secondary chamber 120 and then flow into the primary chamber 36 until the desired level is reached. During filling of the primary chamber 36, gas above the blood level 126 must be removed to prevent pressurization within the apparatus 20 which would otherwise terminate the blood flow. Thereafter, the exit conduit 92 can be opened to maintain the rate of blood flow out the exit conduit 92 which is equal to the rate of blood flow in through the inlet conduit 48.

As can be appreciated from the description above, orientation of the bubble trap apparatus 20 assures correct operation and prevents bubbles from returning to the patient. The correct orientation requires that the longitudinal axis of the housing 32 be substantially vertical, with the upper end 38 of the housing 32 positioned over the lower end 40 of the housing 32.

In the preferred embodiment, the housing 32 and cap 35 are constructed from polyvinyl chloride. The diverter is constructed from polyvinyl chloride or polyethylene.

An alternate embodiment of an improved bubble trap apparatus 20' is shown in FIGS. 7, 8 and 9. The apparatus 20' includes similar features as those of the apparatus 20 which are referenced by like primed numerals. The apparatus 20' shown in FIGS. 7, 8 and 9 is preferably formed of polyvinyl chloride and comprises three primary components, a housing 32', a cap 35' and diverter 34'. The housing 32' has an upper end 38' and a lower end 40', and the housing 32' defines a primary chamber 36' through which blood which has been introduced into the apparatus 20' flows before exiting the apparatus. The diverter 34' is defined by an extension 130 formed in the side of the housing 32'. As a result of the extension 130 formed in the housing 32', the housing 32' in cross section near its upper end 38' is substantially ovoid (FIG. 9). The cap 35' is also substantially ovoid and is adapted to be frictionally engaged and retained on the upper end 38' of the housing 32'.

The extension 130 defines a container 111' having a container base 118'. The container 111' defines a secondary chamber 120' of the primary chamber 36' which is in fluid communication with the primary chamber 36'. An inside wall 124' (FIG. 8) of the container 111' is integral with the inner wall 82' of the housing 32'. A portion 132 of the inner housing wall 82' extends between the primary chamber 36' and the secondary chamber 120' to define a container rim 116' on one side of the periphery of the secondary chamber over which blood in the secondary chamber 120' flows into the primary chamber 36'.

An inlet port 44' is formed in the cap 35'. An inlet coupling 46' surrounds the inlet port 44' and extends upward therefrom. The inlet coupling 46 receivably retains and is solvent bonded to an inlet conduit 48' in which blood is flowing after treatment in the extracorporeal treatment system to which the apparatus 20' is attached.

An inlet tube 52' having a tip 54' surrounds the inlet port 44' and depends from the cap 35' into the secondary chamber 120'. The tube 52' is of a predetermined length such that when the cap 35' is installed on the upper end 38' of the housing 32', the tip 52' is adjacent to and spaced apart from the container base 118'. Also formed in the cap 35' are first and second apertures 56' and 58' from which first and second couplings 60' and 62' extend, respectively, for purposes previously described.

An exit port 88' through which blood in the primary chamber 36' exits the apparatus 20' is formed at the lower end 40' of the housing 32'. An exit coupling 90' surrounds the exit port 88' and depends from the housing 32'. The exit coupling 90' receivably retains and is solvent bonded to an exit conduit 92' through which blood exiting the exit port 88' is returned to the patient undergoing extracorporeal treatment.

A lower seat 94' is formed along the inner wall 82' of the housing 32'. The diameter of the lower seat 94' is predetermined to receivably retain a filter 96'. The filter 96' is formed in the shape of a hollow, truncated cone. Perforations 100' formed in the side 98' of the filter 96' allow blood to pass from the primary chamber 36' through the filter 96', out the exit port 88'. The perforations 100' are small enough to block particulate matter larger than a predetermined site such as blood clots and foreign materials from passing into the exit port 88' and returning to the patient.

Diversion and redirection of the blood as it passes through the bubble trap apparatus 20' promotes separation of bubbles present in the blood while the blood is present in the primary and secondary chambers 36' and 120'. The blood is forced to reverse direction as it exits the inlet tube 52' by deflection off of the inner wall 124' of the container 111'. Thereafter, the blood travels upward toward the surface 126' of the blood in the container 111'. When blood flowing upward through the secondary chamber 120' reaches a height at or above the container rim 116', gravity and laminar flow encourage the blood to flow into the primary chamber 36'. The reversal of the direction of blood flowing down into the primary chamber 36' further encourages bubbles in the blood to separate from the blood and rise to the surface 126' of the blood. The blood then flows down through the primary chamber 36', though the filter 96' and out the exit port 88', for return to the patient.

During use of the apparatus 20' it is preferred that the upper blood surface 126' in the primary chamber 36' be maintained at a level substantially above the container rim 116'. This allows blood introduced out the inlet tube 52' into the container 111' to flow upward over the container rim 116' in a sufficiently large flow path to prevent splattering when the blood is flowing over the container rim 116'.

Proper orientation of the bubble trap apparatus 20' is important in order to assure its correct operation and to prevent bubbles from returning to the patient. The correct orientation requires that the longitudinal axis of the housing 32' be substantially vertical, with the upper end 38' of the housing 32' positioned over the lower end 40' of the housing.

Presently preferred embodiments of the present invention and many of its improvements have been described with a degree of particularity. It should be understood that the present invention is defined by the spirit and scope of the following claims.

What is claimed is:

1. A method of removing bubbles from blood flowing through a bubble trap apparatus in a circuit comprising the steps of:

provviding a bubble trap apparatus comprising a housing defining an elongated, substantially vertical primary chamber and having an upper housing end and a lower housing end;

maintaining an upper blood surface of the blood in the primary chamber intermediate between the upper and lower housing ends;

introducing blood in a downward direction into the primary chamber below the upper blood surface and above the lower housing end;

redirecting the downwardly flowing blood in the primary chamber to flow in a substantially upward direction;

separating bubbles in the blood;

allowing the bubbles to rise to the upper blood surface;

redirecting the upwardly flowing blood to flow in a substantially downward direction, to provide further opportunity for bubbles in the blood to separate from the blood and rise to the upper blood surface;

collecting the blood near the lower housing end; and collecting the bubbles above the upper blood surface.

2. The method of claim 1 further comprising the steps of:

disposing a container within the primary chamber to define a secondary chamber into which the blood is introduced; and filling the secondary chamber with blood.

3. The method of claim 1 wherein the steps of redirecting the blood flow downward and redirecting the blood flow upward are carried out by means of a container disposed within the primary chamber below the upper blood surface.

4. The method of claim 1 wherein the steps of redirecting the blood flow upward and redirection the blood flow downward are carried out by means of a container disposed adjacent to the primary chamber.

5. The method of claim 1 wherein the step of redirecting the downwardly flowing blood in the primary chamber to flow in a substantially upward direction involves the redirection of substantially all of the downwardly flowing blood.

6. The method of claim 1 wherein the step of maintaining the upper blood surface in the primary chamber intermediate between the upper and lower housing ends is performed both before and after the blood introducing step.

* * * * *